United States Patent [19]

Thelosen

[11] Patent Number: 5,339,350
[45] Date of Patent: Aug. 16, 1994

[54] X-RAY APPARATUS COMPRISING WHEELS PROVIDED WITH CABLE DEFLECTOR

[75] Inventor: Jacobus A. Thelosen, Eindhoven, Netherlands

[73] Assignee: U.S. Philips Corporation, New York, N.Y.

[21] Appl. No.: 164,241

[22] Filed: Dec. 9, 1993

[30] Foreign Application Priority Data

Dec. 9, 1992 [EP] European Pat. Off. ........ 92203823.7

[51] Int. Cl.⁵ .............................................. A61B 6/10
[52] U.S. Cl. ..................... 378/198; 378/194; 378/210
[58] Field of Search ............... 378/196, 197, 198, 193, 378/194, 204, 210

[56] References Cited

U.S. PATENT DOCUMENTS

| 4,387,468 | 6/1983 | Fenn et al. | 378/198 |
| 4,887,287 | 12/1989 | Cobben | 378/198 |
| 4,977,588 | 12/1990 | Van Der Ende | 378/196 |

Primary Examiner—David P. Porta
Assistant Examiner—Don Wong
Attorney, Agent, or Firm—Jack D. Slobod

[57] ABSTRACT

An X-ray apparatus includes a frame (1, 3, 5) which supports at least an X-ray source (7) and an X-ray detector (9) and is attached to a base (13) which is provided with wheels (19, 21) enabling displacement of the apparatus on an approximately horizontal floor surface. In order to prevent cables lying on the floor from colliding with the wheels (19, 21) during displacement, so that the wheels could be blocked, each of the wheels (19, 21) includes a cable deflector which consists of an approximately horizontally arranged collar (25) which is made of a rigid material and which encloses the wheel at a distance of less than 10 mm from the floor surface (39).

9 Claims, 2 Drawing Sheets

X-RAY APPARATUS COMPRISING WHEELS PROVIDED WITH CABLE DEFLECTOR

BACKGROUND OF THE INVENTION

1. Field of the Invention

The invention relates to an X-ray apparatus, comprising a frame which supports at least an X-ray source and an X-ray detector and is attached to a base which comprises wheels enabling the apparatus to be displaced on an approximately horizontal floor surface.

2. Description of the Related Art

An X-ray apparatus of this kind is known, for example from U.S. Pat. Nos. 4,887,287 or 4,977,588. The advantage of such apparatus resides in the fact that they are mobile and can hence be readily moved to any desired position relative to a patient on a bed or a rigidly arranged patient table. Generally speaking, the apparatus is connected, via a number of electric cables, to a power supply source and to auxiliary equipment such as equipment for the storage and processing of data. It is a problem that during displacement of the apparatus the wheels are often blocked by the cables lying on the floor. Removing each time the cables lying in front of the wheels requires a comparatively large effort from the operators.

SUMMARY OF THE INVENTION

It is an object of the invention to provide an X-ray apparatus of the kind set forth where cables lying on the floor can be kept away from the wheels without intervention by the operators. To this end, the X-ray apparatus in accordance with the invention is characterized in that each of the wheels is provided with a cable deflector which comprises an approximately horizontally arranged collar which is made of a rigid material and which encloses the wheel at a distance of less than 10 mm from the floor surface. The invention is based on the idea that a rigid object moving in front of the wheel with a slight clearance from the floor surface will push a cable lying on the floor ahead of itself so that the wheel will not touch the cable. The clearance between the collar and the floor surface is preferably chosen so as to be smaller than the diameter of the cable. Therefore, thin cables require a smaller clearance than thick cables. It has been found that a clearance of approximately 3 mm offers satisfactory results for the commonly used cables. In that case small irregularities of the floor surface will not come into contact with the collar. The collar may be closed all around or it may consist of one or more segments.

Generally speaking, the apparatus will have to be displaced over rather long distances from time to time, for example to another room. In such cases the apparatus often has to pass thresholds and be moved into and out of elevators. Such operations may be impeded by the collars arranged in such a low position. In order to mitigate this drawback, a preferred embodiment of the device in accordance with the invention is characterized in that the collar is attached to the base so as to be displaceable in the vertical direction, attachment being such that the collar has at least a first stable position, at a distance of at least one and at the most ten mm from the floor surface, and a second stable position at a distance of at least 25 mm from the floor surface. During normal operation of the apparatus, the collars can thus be set to the first position and during transport they can be set to the second position. A simple and practical embodiment of this alternative version is characterized in that the attachment of the collar to the base comprises a combination of a vertical guide trough and a slide which is slidable therein, the first stable position being defined by an abutment which limits the displacement of the slide in the downward direction, the second stable position being defined by a locking device.

Because the collars are situated near the floor surface, it would be convenient for the operators if they could easily adjust the height of the collars by foot. In order to enable such adjustment, a further embodiment is characterized in that on the outer circumference of the collar there is provided a profile so as to facilitate application of a vertically directed force to the collar by foot. The profile may comprise, for example a number of horizontally extending grooves having a width of approximately 3 mm or comprise a horizontal projection provided near the upper side of the collar.

BRIEF DESCRIPTION OF THE DRAWING

These and other aspects of the invention will be described with reference to the drawing, wherein.

DETAILED DESCRIPTION OF THE PREFERRED EMBODIMENTS

Figure 1:
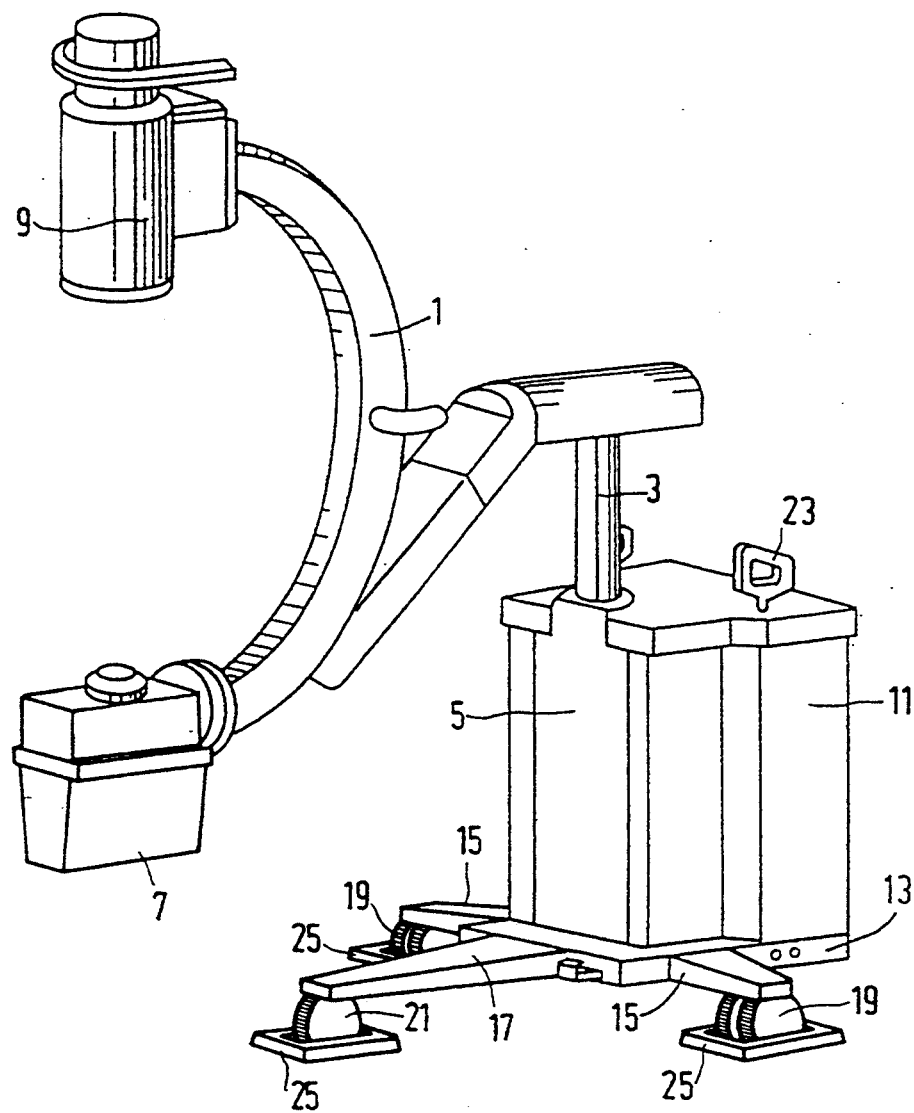
FIG. 1 is a simplified view of an embodiment of an X-ray apparatus in accordance with the invention.

FIG. 1 shows a mobile X-ray apparatus which comprises a frame which in this case consists of a C-arc 1 which is secured to a cylindrical rod 3 which is mounted in a pedestal-like portion 5 so that its height is adjustable. An X-ray source 7 and an X-ray detector 9 are mounted at the free ends of the C-arc so that they face one another. The pedestal-like portion 5 and an electrical module 11 are mounted on a mobile base 13 which comprises two laterally projecting arms 15 and a forward projecting arm 17. Near the ends of each lateral arm 15 there is mounted a pair of wheels 19, whereas near the end of the front arm 17 a single wheel 21 is mounted. The wheel pairs 19 can be steered, for example by means of a steering handle 23, and the front wheel 21 may be a caster. Thanks to the wheels 19, 21, the apparatus can be readily displaced on a substantially horizontal floor surface which is not shown in FIG. 1. The wheels 19, 21 could then be blocked by cables lying on the floor surface (not shown) and serving, for example to connect the electric module 11 to the electric mains and to image and data processing auxiliary apparatus. In order to prevent such blocking, each of the wheels 19, 21 is provided with a cable deflector in the form of an approximately horizontally arranged collar 25 which encloses the wheel and which is situated at a small distance from the floor surface. This distance is smaller than the thickness of the cables associated with the apparatus. A clearance of at least one mm from the floor surface is desired so as to prevent the collars 25 from colliding with small surface irregularities, for example seams in the floor covering. It has been found in practice that a clearance of approximately 3 mm offers suitable results. The collars 25 are made of a rigid material (for example aluminium) in order to prevent deformation of the collars upon collision with the cables, so that a cable could become jammed under the collar.

Figure 2:
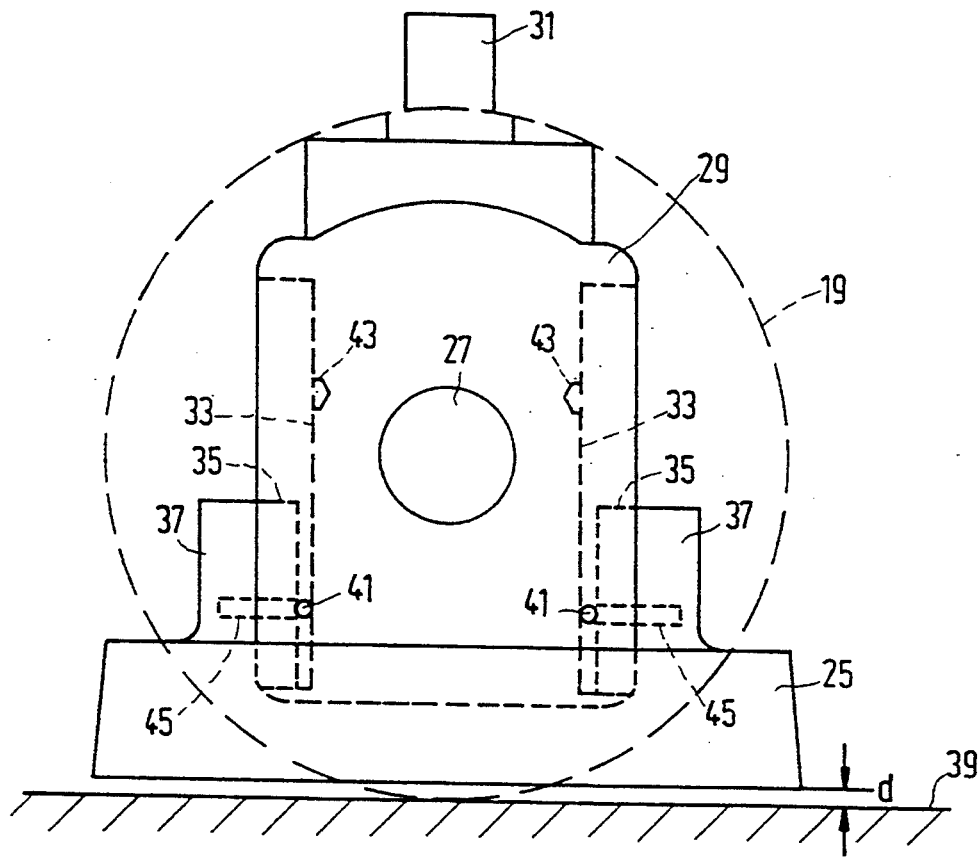
FIG. 2 is a diagrammatic side elevation of a component of the apparatus shown in FIG. 1, and FIGS. 3 and 4 show details of feasible embodiments of a part of the component shown in FIG. 2.

FIG. 2 is a side elevation at an increased scale of one of the cable deflectors. The wheel 19 is denoted by a dashed line so as to enable more detailed representation of the attachment of the collar 25. The wheels 19 are rotatable about a shaft 27 which is journalled in a wheel holder 29 which can be secured to the end of one of the arms 15 by way of a connection pin 31. In the sides of the wheel holder 29 there are recessed vertically extending guide troughs 33 (denoted by dashed lines) in which slides 35 (also denoted by dashed lines) which form part of mounting supports 37, connected to the upper side of the collar 25, are slidable. In FIG. 2 the collar 25 occupies a first stable position in which the clearance d between the collar and the floor surface 39 amounts to approximately 3 mm. This position is defined by an abutment which is formed by cooperation between the lower end of the slide 35 and the lower end of the guide trough 33. The slide 35 is pressed against the lower end of the guide trough 33 by gravity so that the described position is stable indeed. Evidently, it is alternatively possible to secure the slide to the wheel holder and the guide trough to the mounting support.

The collar 25 can be slid upwards from the low position shown in FIG. 2 until it reaches a second stable position in which the distance between the collar and the floor surface is so large that the apparatus can readily pass large obstacles, such as thresholds, without the collars colliding with these obstacles. To this end, this distance should amount to at least 25 mm. It has been found in practice that a distance of approximately 35 mm offers satisfactory results. The second stable position is defined by a locking device which is formed, in the present embodiment, by a locking ball 41 in each of the mounting supports 37, which ball cooperates with a recess 43 in the bottom of each of the guide troughs 33. The locking ball 41 is movable in the horizontal direction in a bore 45 which is recessed in the mounting support 37 as a cylinder having a horizontal axis. A spring (not shown) in the bore 45 exerts a force on the locking ball 41 which is oriented towards the bottom of the guide trough. Consequently, the locking ball 41 is pressed into the recess 43 when the collar 25 reaches the second stable position. This prevents the collar 25 from dropping down again under the influence of the force of gravity. The collar 25 can only be moved to the first stable position again by deliberately exerting a comparatively large force thereon. This can be done, for example by stepping on the upper side of the collar 25. Evidently, instead of the locking device shown, other known locking devices can also be used, for example a device of the type customarily used for closing doors which comprises a spring bolt which can be unlatched by means of a pedal.

Figure 3:
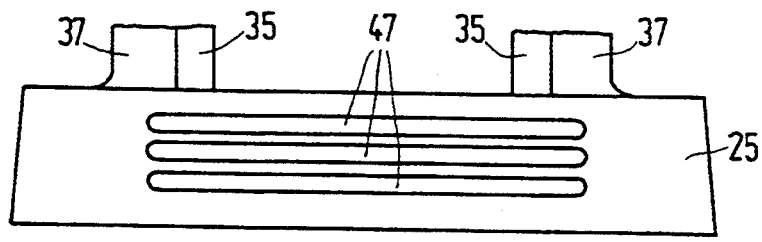
Figure 4:
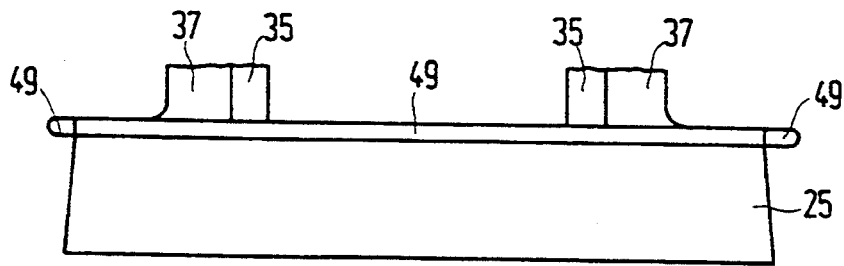

The collar 25 is displaced from the first stable position to the second stable position preferably by foot again. In order to facilitate such displacement, the outer circumference of the collar is preferably provided with a profile offering the foot a given hold. FIGS. 3 and 4 show examples of such profiles. The profile shown in FIG. 3 comprises a number of horizontally extending grooves 47 which have a width of approximately 3 mm and in which the rim of a shoe readily finds a hold. The profile shown in FIG. 4 comprises a number of horizontally oriented projections provided near the upper side of the collar 25, for example in the form of ridges extending along the upper edges. The rim of a shoe can be readily moved underneath one of these projections so as to press the collar 25 upwards.

In the embodiments shown, the collars 25 are formed by closed square or rectangular collars. It is alternatively be possible, however, to construct the collars so as to be open or consisting of one of more segments with large or small gaps between the segments. It is important only that a part of a collar is always situated in front of the relevant wheel in the direction of travel. The shape of the collars is comparatively arbitrary; for example, they may also be round or oval. When the collar 25 is attached to the wheel holder 29 as shown in FIG. 2, existing apparatus can also be simply provided with cable deflectors by replacing the existing wheel holders by wheel holders provided with a collar. Evidently, the cable deflectors can alternatively be mounted directly on the arms 15, 17 of the base 13.

I claim:

1. An X-ray apparatus, comprising a frame which supports at least an X-ray source and an X-ray detector and is attached to a base which comprises wheels enabling the apparatus to be displaced on an approximately horizontal floor surface, characterized in that each of the wheels is provided with a cable deflector which comprises an approximately horizontally arranged collar which is made of a rigid material and which encloses the wheel at a distance of less than 10 mm from the floor surface.

2. An X-ray apparatus as claimed in claim 1, characterized in that the collar is attached to the base so as to be displaceable in the vertical direction, attachment being such that the collar has at least a first stable position, at a distance of at least one and at the most ten mm from the floor surface, and a second stable position at a distance of at least 25 mm from the floor surface.

3. An X-ray apparatus as claimed in claim 2, characterized in that the attachment of the collar to the base comprises a combination of a vertical guide trough and a slide which is slidable therein, the first stable position being defined by an abutment which limits the displacement of the side in the downward direction, the second stable position being defined by a locking device.

4. An X-ray apparatus as claimed in claim 2, characterized in that on the outer circumference of the collar there is provided a profile so as to facilitate application of a vertically directed force to the collar by foot.

5. An X-ray apparatus as claimed in claim 4, characterized in that the profile comprises a number of horizontally extending grooves having a width of approximately 3 mm.

6. An X-ray apparatus as claimed in claim 4, characterized in that the profile comprises a horizontal projection provided near the upper side of the collar.

7. An X-ray apparatus as claimed in claim 3, characterized in that on the outer circumference of the collar there is provided a profile so as to facilitate application of a vertically directed force to the collar by foot.

8. An X-ray apparatus as claimed in claim 7, characterized in that the profile comprises a number of horizontally extended grooves having a width of approximately 3 mm.

9. An X-ray apparatus as claimed in claim 7, characterized in that the profile comprises a horizontal projection provided near the upper side of the collar.

* * * * *